(12) United States Patent
Wolf et al.

(10) Patent No.: US 12,378,175 B2
(45) Date of Patent: Aug. 5, 2025

(54) PROCESS FOR THE PREPARATION OF ETHYLENE GLYCOL

(71) Applicant: SHELL USA, INC., Houston, TX (US)

(72) Inventors: Koen Wolf, Amsterdam (NL); Timothé Johannes Olthof, Amsterdam (NL); Eugene Marie Godfried Andre Van Kruchten, Amsterdam (NL); Daniel Maurice Lorimer, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 433 days.

(21) Appl. No.: 17/775,374

(22) PCT Filed: Dec. 7, 2020

(86) PCT No.: PCT/EP2020/084827
§ 371 (c)(1),
(2) Date: May 9, 2022

(87) PCT Pub. No.: WO2021/115997
PCT Pub. Date: Jun. 17, 2021

(65) Prior Publication Data
US 2022/0396538 A1    Dec. 15, 2022

(30) Foreign Application Priority Data
Dec. 11, 2019   (EP) ...................................... 19215355

(51) Int. Cl.
*C07C 29/152*   (2006.01)
(52) U.S. Cl.
CPC .................................. *C07C 29/152* (2013.01)

(58) Field of Classification Search
CPC ...... C07C 29/152; C07C 31/202; C07C 29/12
See application file for complete search history.

(56) References Cited

U.S. PATENT DOCUMENTS 6,080,897 A    6/2000   Kawabe
6,187,972 B1   2/2001   Kawabe et al.
(Continued)

OTHER PUBLICATIONS

International Search Report and Written Opinion received for PCT Patent Application No. PCT/EP2020/084827, mailed on Feb. 3, 2021, 8 pages.

(Continued)

*Primary Examiner* — Jafar F Parsa
(74) *Attorney, Agent, or Firm* — SHELL USA, INC.

(57) ABSTRACT

The invention relates to a process for the preparation of ethylene glycol, comprising: a) converting a stream comprising ethylene oxide in the presence of a catalyst and carbon dioxide in two or more reactors to a stream comprising ethylene carbonate; and b) converting ethylene carbonate from the stream comprising ethylene carbonate obtained in step a) in the presence of a catalyst in one or more reactors to a stream comprising ethylene glycol and a stream comprising carbon dioxide, wherein the inlet stream or inlet streams to the last reactor of the two or more reactors used in step a) is or are not heated; and wherein an outlet stream comprising ethylene carbonate from the last reactor of the two or more reactors used in step a) is sent, without recycling a portion thereof to the last reactor used in step a), to the first reactor of the one or more reactors wherein step b) is carried out.

8 Claims, 3 Drawing Sheets

(56) References Cited

U.S. PATENT DOCUMENTS

| | | |
|---|---|---|
| 7,453,014 B2 | 11/2008 | Harmsen et al. |
| 8,530,706 B2 | 9/2013 | Van Milligen et al. |
| 8,695,367 B2 | 4/2014 | Van Geel et al. |
| 8,802,900 B2 | 8/2014 | Smaardijk et al. |
| 10,815,176 B2 | 10/2020 | Bastings et al. |
| 2012/0136178 A1* | 5/2012 | Smaardijk ............... C07C 29/64 568/867 |

OTHER PUBLICATIONS

Office Action Received for Indian Application No. 202247027399, Mailed on Mar. 28, 2025, 05 Pages(05 Pages of Official Copy).

* cited by examiner

PROCESS FOR THE PREPARATION OF ETHYLENE GLYCOL

CROSS REFERENCE TO RELATED APPLICATIONS

This is a National stage application of International application No PCT/EP2020/084827, filed 7 Dec. 2020, which claims priority of EP application Ser. No. 19/215,355.9, filed 11 Dec. 2019 which is incorporated herein by reference in its entirety.

FIELD OF THE INVENTION

The present invention relates to a process for the preparation of ethylene glycol from ethylene oxide via ethylene carbonate.

BACKGROUND OF THE INVENTION

Ethylene glycol is used as a raw material in the manufacture of polyester fibres, polyethylene terephthalate (PET) plastics and resins. It is also incorporated into automobile antifreeze liquids.

Ethylene glycol is typically prepared from ethylene oxide, which may in turn be prepared from ethylene. In one well-known process, ethylene oxide is catalytically reacted with carbon dioxide to produce ethylene carbonate (carboxylation). The ethylene carbonate is subsequently hydrolysed to provide ethylene glycol and carbon dioxide. Reaction via ethylene carbonate significantly improves the selectivity of ethylene oxide conversion to ethylene glycol compared to the known process wherein ethylene oxide is reacted with a large excess of water to form ethylene glycol in a non-catalytic process.

WO2012072628 discloses such process for the preparation of ethylene glycol from ethylene oxide via ethylene carbonate. In FIG. 1 of WO2012072628, two carboxylation reactors (4) connected in series are shown. An ethylene carbonate stream (6) from the second carboxylation reactor (4) is passed to a carbon dioxide separation vessel (7). The ethylene carbonate stream is then fed into the first of two hydrolysis reactors (9) connected in series, where it is converted to an ethylene glycol stream (10). Carbon dioxide produced in the first hydrolysis reactor (9) and carbon dioxide separated in carbon dioxide separation vessel (7) are recycled via recycle stream (8).

The process as shown in FIG. 1 of WO2012072628 is characterized in that each of the product streams from both carboxylation reactors (4) is split into two sub-streams and one of the split sub-streams is recycled to the same carboxylation reactor. According to WO2012072628, such liquid recycle over each of the carboxylation reactors provides temperature control to those reactors through heating or cooling the recycle stream. This implies that the split recycle stream is either heated or cooled before recycling, for example by means of a heat exchanger.

It is an object of the present invention to provide a process for the preparation of ethylene glycol from ethylene oxide via ethylene carbonate, which enables performing the carboxylation step of making ethylene carbonate in a technically advantageous and efficient way. Such technically advantageous process would preferably result in a lower energy demand and/or lower capital expenditure, while still achieving a satisfactory conversion of ethylene oxide.

SUMMARY OF THE INVENTION

It was found that the above-mentioned object may be achieved in a process wherein the inlet stream or inlet streams to at least one reactor of the reactor(s) used in the above-mentioned carboxylation step is or are not heated.

Specifically, the present invention relates to a process for the preparation of ethylene glycol, comprising:
a) converting a stream comprising ethylene oxide in the presence of a catalyst and carbon dioxide in two or more reactors to a stream comprising ethylene carbonate; and
b) converting ethylene carbonate from the stream comprising ethylene carbonate obtained in step a) in the presence of a catalyst in one or more reactors to a stream comprising ethylene glycol and a stream comprising carbon dioxide,
wherein the inlet stream or inlet streams to at least the last reactor of the two or more reactors used in step a) is or are not heated; and
wherein an outlet stream comprising ethylene carbonate from the last reactor of the two or more reactors used in step a) is sent, without recycling a portion thereof to the last reactor used in step a), to the first reactor of the one or more reactors wherein step b) is carried out.

DETAILED DESCRIPTION OF THE INVENTION

Figure 1:
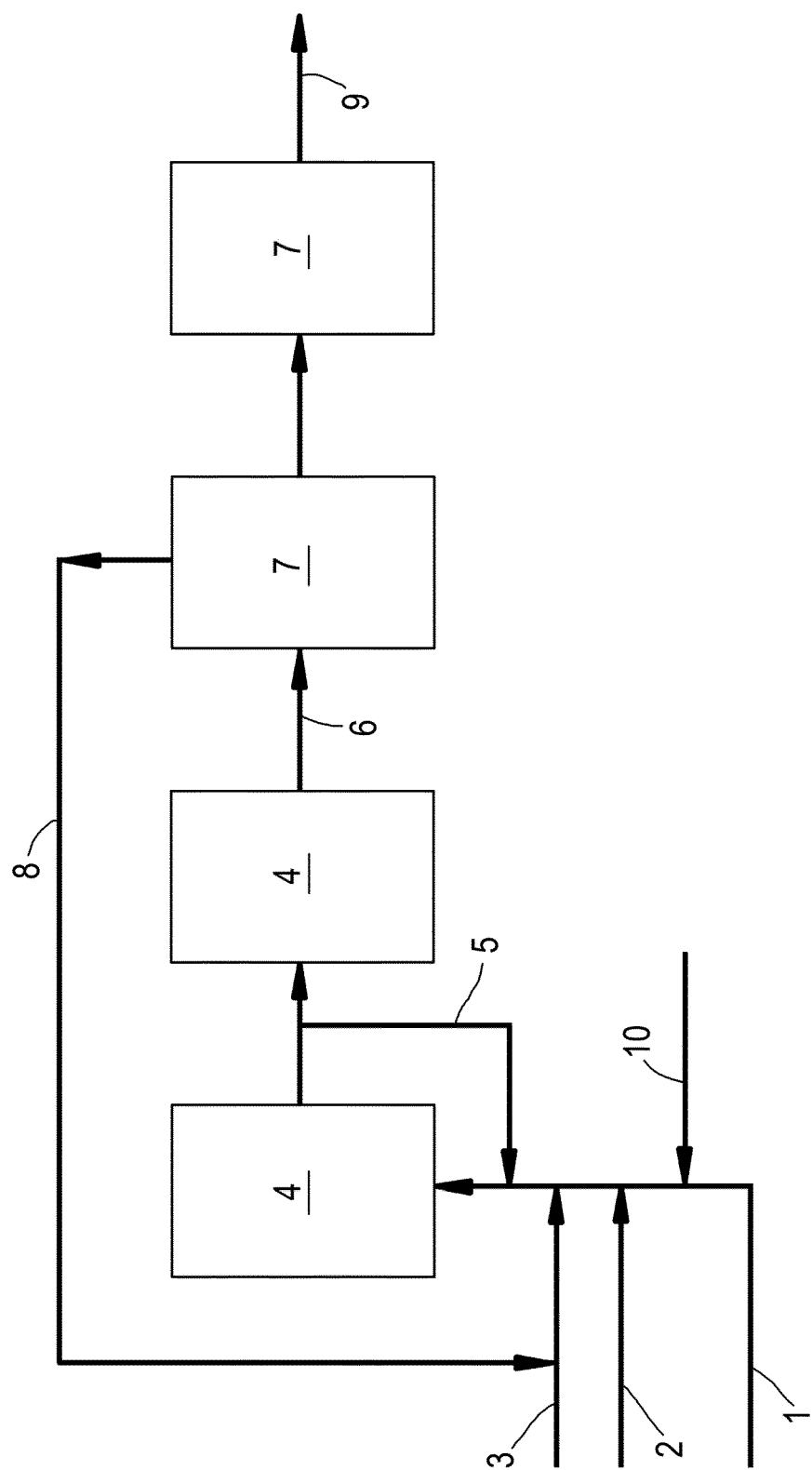
FIG. 1 shows an embodiment of the present invention.

The process of the present invention comprises various steps, as described hereinbelow. Said process may comprise one or more intermediate steps between these steps. Further, said process may comprise one or more additional steps preceding step a) and/or following step b).

While the process of the present invention and mixtures or streams used in said process are described in terms of "comprising", "containing" or "including" one or more various described steps and components, respectively, they can also "consist essentially of" or "consist of" said one or more various described steps and components, respectively.

In the context of the present invention, in a case where a mixture, stream or catalyst comprises two or more components, these components are to be selected in an overall amount not to exceed 100%.

Further, where upper and lower limits are quoted for a property then a range of values defined by a combination of any of the upper limits with any of the lower limits is also implied.

The present invention concerns a process for the preparation of ethylene glycol from ethylene oxide via ethylene carbonate, which comprises the following steps: a) converting a stream comprising ethylene oxide in the presence of a catalyst and carbon dioxide in two or more reactors to a stream comprising ethylene carbonate; and b) converting ethylene carbonate from the stream comprising ethylene carbonate obtained in step a) in the presence of a catalyst in one or more reactors to a stream comprising ethylene glycol and a stream comprising carbon dioxide.

The present invention is characterized in that the inlet stream or inlet streams to at least the last reactor of the two or more reactors used in step a) is or are not heated. This implies that no external heat is transferred to said inlet stream(s) before entering said reactor(s). In the present invention, heat originating from an outlet stream from a reactor which is upstream of said reactor(s), in a series of two or more reactors, may be contained in said inlet stream (s) to said reactor(s) used in step a) for which the inlet stream or inlet streams are not heated. Within the present specification, said inlet stream or inlet streams comprises or comprise any stream or streams that is or are fed to a reactor, including but not limited to (i) an outlet stream from another reactor which is upstream of the reactor, and (ii) a recycle stream which is a sub-stream split off from the outlet stream from the reactor.

Further, it is preferred that the inlet stream or inlet streams to at least one reactor of the two or more reactors used in step a) is or are not cooled. This implies that preferably no heat is removed from said inlet stream(s) before entering said reactor(s). Within the present specification, heat exchange of a stream with the environment is not considered as cooling or heating such stream.

As shown in the Examples below, such heating of the above-mentioned inlet stream(s) is surprisingly not needed to perform step a) in at least the last reactor of the two or more reactors used in step a). Thus, advantageously, in the present invention no temperature control, as disclosed in above-discussed WO2012072628, is required for at least one reactor of the two or more reactors used in step a).

In step a) of the present process, a stream comprising ethylene oxide is converted in the presence of a catalyst and carbon dioxide to a stream comprising ethylene carbonate. Ethylene oxide is reacted with carbon dioxide to form ethylene carbonate. This may also be referred to as "carboxylation". The stream comprising ethylene oxide may also comprise water.

In the present process, step a) is carried out in two or more reactors, which may also be referred to as "carboxylation reactors".

Unless indicated otherwise, in the present specification, "carboxylation" refers to the reaction of ethylene oxide with carbon dioxide to ethylene carbonate and "hydrolysis" refers to the reaction of ethylene carbonate with water to ethylene glycol and carbon dioxide. In the two or more carboxylation reactors used in step a), hydrolysis may also take place in addition to carboxylation. Such hydrolysis may also involve the reaction of ethylene oxide with water to ethylene glycol.

In a first embodiment, step a) is carried out in two or more reactors and the inlet stream or inlet streams to at least the last reactor is or are not heated.

Preferably, in a second embodiment, step a) is carried out in two or more, preferably two, reactors connected in series, and the inlet stream or inlet streams to the last reactor of the two or more reactors is or are not heated. Preferably, in the first and in the second embodiment, at least a portion of the outlet stream or outlet streams from the first reactor of the two or more reactors used in step a) is or are cooled.

It is preferred, in the first and in the second embodiment, that step a) is carried out in two reactors connected in series. In such case, the inlet stream to the second reactor used in step a), said inlet stream comprising ethylene oxide originating from the first reactor, may have a concentration of such ethylene oxide originating from the first reactor which is greater than 0 up to 30 wt. %, preferably of from 0.1 to 20 wt. %, more preferably of from 0.5 to 10 wt. %, most preferably of from 1 to 8 wt. %. By said "ethylene oxide originating from the first reactor" reference is made to ethylene oxide that was fed to the first reactor but not to the second reactor. Further, in such case, the inlet stream to the first reactor used in step a), said inlet stream comprising fresh ethylene oxide, may have a concentration of such fresh ethylene oxide which is of from 10 to 50 wt. %, preferably of from 15 to 45 wt. %, more preferably of from 20 to 40 wt. %, most preferably of from 25 to 35 wt. %. By said "fresh ethylene oxide" reference is made to ethylene oxide that was not fed to said first and second reactors used in step a).

Further, preferably, in the first and in the second embodiment, an outlet stream comprising ethylene carbonate from the last reactor of the two or more reactors used in step a) is sent, without recycling a portion thereof to the last reactor used in step a), to the first reactor of the one or more reactors wherein step b) is carried out. This has the advantage that no equipment is needed for recycling an outlet stream over such last reactor, including for example a vapour/liquid separator, a circulation pump and a recycle line (i.e. pipes). Such process wherein there is no recycle over a reactor may also be referred to as a "once-through" process. An advantage of such process is that the residence time of ethylene oxide in the reactor may be increased, which may positively affect the ethylene oxide conversion.

Further, preferably, in the first and in the second embodiment, an outlet stream from the first reactor of the two or more reactors used in step a) is split, one split sub-stream is sent to the next reactor in series and another split sub-stream is recycled to the first reactor. It is preferred that the latter split sub-stream that is recycled to the first reactor is cooled before recycling.

Still further, preferably, in the first and in the second embodiment, the inlet stream or inlet streams to the last reactor of the two or more reactors is or are not cooled.

In a case where (i) in the present specification reference is made to a feature or embodiment relating to "the last reactor used in step a)" and (ii) step a) is carried out in three or more reactors connected in series, it is preferred that such feature or embodiment applies to one or more, preferably all, of the second, third and any further reactors, but not to the first reactor.

The two or more carboxylation reactors used in step a) are suitably two-phase flow reactors. Further, said reactors may be operated at a pressure in the range of from 0.5 to 3.0 MPa and a temperature in the range of from 50 to 180° C., preferably of from 80 to 180° C., most preferably of from 80 to 150° C.

In the above-mentioned second embodiment, it is preferred that the inlet stream to the last reactor of the two or more reactors, such inlet stream comprising ethylene oxide originating from the preceding reactor, has a relatively high temperature, preferably of from 50 to 180° C., more preferably of from 80 to 150° C., most preferably of from 100 to 135° C. By said "ethylene oxide originating from the preceding reactor" reference is made to ethylene oxide that was fed to the preceding reactor but not to the last reactor. Further, in the above-mentioned first and second embodiment, it is preferred that the temperature of the outlet stream from the last reactor is higher than the temperature of said inlet stream to the last reactor. Preferably, the temperature of the outlet stream from the last reactor is of from 70 to 180° C., more preferably of from 90 to 170° C., most preferably of from 120 to 155° C.

Further, optionally, steam may be injected into the one carboxylation reactor or into at least one, preferably the second or last, of the two or more carboxylation reactors to increase the temperature. Such steam injection may be used for start-up, or during continuous operation in case the conversion of ethylene oxide in such reactor is insufficient or incomplete.

In step a), carbon dioxide and a catalyst are also provided. Carbon dioxide and catalyst streams may be provided to the carboxylation reactor(s) separately from the stream comprising ethylene oxide. Preferably, carbon dioxide and catalyst streams are combined with the stream comprising ethylene oxide prior to the latter stream being supplied to the carboxylation reactor(s).

In step b) of the present process, ethylene carbonate from the stream comprising ethylene carbonate obtained in step a) is converted in the presence of a catalyst to a stream comprising ethylene glycol and a stream comprising carbon dioxide. In specific, in step b), at least a portion of the stream comprising ethylene carbonate obtained in step a) is converted to a stream comprising ethylene glycol and a stream comprising carbon dioxide.

The stream comprising ethylene carbonate obtained in step a) may additionally comprise ethylene glycol. This results from any hydrolysis taking place in the carboxylation reactor(s), including the reaction of ethylene carbonate with water to ethylene glycol and carbon dioxide and/or the reaction of ethylene oxide with water to ethylene glycol. In specific, the stream comprising ethylene carbonate obtained in step a) may comprise ethylene carbonate in an amount of from 5 to 90 wt. %, or of from 5 to 40 wt. %, or of from 10 to 30 wt. %; and ethylene glycol in an amount of from 0 to 80 wt. %, or of from 40 to 80 wt. %, or of from 50 to 70 wt. %. Further, the stream comprising ethylene carbonate obtained in step a) may still comprise unconverted ethylene oxide. Suitably, the amount of ethylene oxide in the stream comprising ethylene carbonate obtained in step a) is of from 0 to 3 wt. %, more suitably of from 0.01 to 3 wt. % or 0.05 to 2 wt. % or 0.1 to 2 wt. % or 0.1 to 1 wt. % or 0.1 to 0.5 wt. %. Still further, the stream comprising ethylene carbonate obtained in step a) comprises carbon dioxide. This concerns carbon dioxide that was not converted in step a) and/or carbon dioxide that was released as a result of the hydrolysis of ethylene carbonate in step a). Suitably, the amount of carbon dioxide in the stream comprising ethylene carbonate obtained in step a) is of from 1 to 20 wt. %, more suitably of from 5 to 15 wt. %

In the present process, step b) is carried out in one or more reactors, which may also be referred to as "hydrolysis reactors". It is preferred that the stream comprising ethylene carbonate sent to the first of the one or more hydrolysis reactors used in step b) comprises no ethylene oxide or at most 2 wt. % of ethylene oxide, more preferably at most 1 wt. % of ethylene oxide, most preferably at most 0.5 wt. % of ethylene oxide.

Prior to being supplied to the one or more hydrolysis reactors, the stream comprising ethylene carbonate obtained in step a) may be subjected to a carbon dioxide separation step in a carbon dioxide separation vessel. In such step, carbon dioxide is removed from the stream comprising ethylene carbonate, and the separated carbon dioxide may then be recycled to the two or more carboxylation reactors. However, in a preferred embodiment of the process of the present invention, no carbon dioxide is separated from the stream comprising ethylene carbonate obtained in step a) prior to being fed to step b). This has the advantage that less equipment is needed for carbon dioxide separation, including for example a vapour/liquid separator, a cooler and pipes. Further, advantageously, the carbon dioxide from step a) may be removed, in a single step, together with the carbon dioxide that is produced during step b), as further described below.

In specific, it is preferred in the above-mentioned first and second embodiment that an outlet stream comprising ethylene carbonate from the last reactor of the two or more reactors used in step a) is sent directly, without recycling a portion thereof to the last reactor used in step a), to the first reactor of the one or more reactors wherein step b) is carried out. "Directly" implies for example that no carbon dioxide is separated from the stream comprising ethylene carbonate obtained in step a) prior to being fed to step b), as described above.

The one or more hydrolysis reactors may be any suitable reactor type. If there is more than one hydrolysis reactor it is preferred that the hydrolysis reactors are connected in series. Preferably, step b) is carried out in two or more, preferably two, reactors connected in series. Optionally, steam is injected into at least one of the one or more hydrolysis reactors.

At least one of the one or more hydrolysis reactors may be a baffled reactor, wherein the baffled reactor may have at least 3, suitably at least 4 compartments, the compartments being formed by the baffle(s) and the baffle(s) providing a sinuous route for reaction fluid through the reactor.

Carbon dioxide is produced in the one or more hydrolysis reactors used in step b) and is separated, together with any unconverted carbon dioxide from step a), as a stream comprising carbon dioxide either directly from the one or more hydrolysis reactors or in a carbon dioxide separation vessel from a product stream leaving the one or more hydrolysis reactors.

In the present invention, the separated stream comprising carbon dioxide resulting from step b) may be condensed in a condenser, for example a cooler, to form a recycle carbon dioxide stream and a condensate stream. Said recycle carbon dioxide stream may be recycled to at least one of the two or more carboxylation reactors.

The temperature in the one or more hydrolysis reactors is typically from 100 to 200° C., preferably from 100 to 180° C. The pressure in the one or more hydrolysis reactors is typically from 0.1 to 3 MPa.

It is preferred that step b) is carried out in two reactors connected in series. In such case, the pressure in the first reactor is preferably higher than the pressure in the second reactor. The pressure in the first reactor may be of from 1 to 3 MPa, suitably of from 1.5 to 2.5 MPa. Further, the pressure in the second reactor may be of from 0.1 to 1 MPa, suitably of from 0.1 to 0.5 MPa. An advantage of having a higher pressure in said first hydrolysis reactor is that for recycling the relatively large amount of carbon dioxide from the first reactor to step a) only a single stage compressor may be required, whereas for recycling the relatively small amount of carbon dioxide from said second hydrolysis reactor to step a) a multistage compressor may be required if such small amount of carbon dioxide is not discarded.

In the above-mentioned preferred embodiment wherein prior to step b) no carbon dioxide is separated from the stream comprising ethylene carbonate obtained in step a), it is further preferred that the one hydrolysis reactor or the first of the two or more hydrolysis reactors used in step b) is provided with a vapour/liquid separator resulting in a vapour stream comprising carbon dioxide and a liquid stream comprising ethylene carbonate. The separated stream comprising carbon dioxide that exits the hydrolysis reactor may then be condensed and recycled as described above. Such vapour/liquid separator in the hydrolysis reactor may be any vapour/liquid separator, for example a vane type inlet device installed in the vapor space (top part) of the inlet region of the hydrolysis reactor. A suitable example of such vane type inlet device is the Schoepentoeter™ or Schoepentoeter Plus™.

Further, the one hydrolysis reactor or the first of the two or more hydrolysis reactors used in step b) may be provided with a heater to heat at least a portion of the stream comprising ethylene carbonate obtained in step a), in specific to heat the separated stream comprising ethylene carbonate coming from the above-mentioned vapour/liquid separator. Further, alternatively, said heater may be omitted and the reactor size may be increased. Still further, alternatively, said heater may be omitted and the temperature of the stream comprising ethylene carbonate obtained in step a) may be increased by reducing any cooling in step a).

In both step a) and step b) of the present process, a catalyst is used. In step a), the catalyst should promote carboxylation, that is to say the reaction of ethylene oxide with carbon dioxide to ethylene carbonate. In step b), the catalyst should promote hydrolysis, that is to say the reaction of ethylene carbonate with water to ethylene glycol and carbon dioxide. The water may originate from the stream comprising ethylene oxide fed to step a) and/or may be fed separately to step a) and/or step b).

The catalyst in step a) may comprise one or more catalysts that promote carboxylation and hydrolysis. If only one catalyst is present, then the catalyst must promote carboxylation and hydrolysis. If two or more catalysts are present, then each catalyst can promote carboxylation or hydrolysis or can promote both reactions, provided that at least one catalyst promotes carboxylation and at least one catalyst promotes hydrolysis. In the present invention, it is preferred that the one or more catalysts that promote carboxylation and hydrolysis is/are homogeneous.

Homogeneous catalysts for use in step a) that are known to promote carboxylation include iodide and bromide catalysts. In the present specification, "iodide catalyst" or "bromide catalyst" refers to a catalyst containing an iodide anion or bromide anion.

The above-mentioned iodide catalyst may be an alkali metal iodide or a phosphonium or ammonium iodide. The alkali metal in said alkali metal iodide may be any alkali metal and may be lithium, sodium, potassium, rubidium or cesium, preferably lithium, sodium or potassium, more preferably sodium or potassium. Most preferably, said alkali metal is potassium. Thus, most preferably, said alkali metal iodide is potassium iodide. Further, said phosphonium or ammonium iodide may be selected from the group consisting of tributylmethylphosphonium iodide, tetrabutylphosphonium iodide, triphenylmethylphosphonium iodide and tributylmethylammonium iodide. Preferably, said phosphonium or ammonium iodide is tributylmethylphosphonium iodide.

Further, the above-mentioned bromide catalyst may be an alkali metal bromide or a phosphonium or ammonium bromide. The alkali metal in said alkali metal bromide may be any alkali metal and may be lithium, sodium, potassium, rubidium or cesium, preferably lithium, sodium or potassium, more preferably sodium or potassium. Most preferably, said alkali metal is potassium. Thus, most preferably, said alkali metal bromide is potassium bromide. Further, said phosphonium or ammonium bromide may be selected from the group consisting of triphenylpropylphosphonium bromide, tetraethylammonium bromide, tetramethylammonium bromide, benzyltriethylammonium bromide and tetrabutylammonium bromide.

Homogeneous catalysts for use in step b) that are known to promote hydrolysis include basic alkali metal salts and alkali metal metalates. A basic alkali metal salt is preferred. Said basic alkali metal salt may be potassium carbonate, potassium hydroxide or potassium bicarbonate, preferably potassium carbonate. Said alkali metal metalate may be potassium molybdate.

Homogeneous catalyst in the stream comprising ethylene glycol from step b) may be separated therefrom and recycled to step a) and/or step b), preferably step a). The catalyst fed to step a) may comprise one or more, preferably two or more, more preferably two, homogeneous catalysts that promote carboxylation and hydrolysis. Preferred homogeneous catalyst systems which may be fed to step a) include a combination of tributylmethylphosphonium iodide and potassium carbonate and a combination of potassium iodide and potassium carbonate.

The process of the present invention is illustrated by FIG. 1.

In the process shown in FIG. 1, an aqueous ethylene oxide stream (1) is mixed with water (2), a catalyst stream (10) and carbon dioxide (3) before being supplied to the first of two carboxylation reactors (4) connected in series. Catalyst stream (10) comprises an iodide catalyst (carboxylation catalyst) and potassium carbonate (hydrolysis catalyst). In the carboxylation reactors (4), ethylene oxide is reacted with carbon dioxide to form ethylene carbonate.

The first carboxylation reactor (4) has a recycle (5) wherein part of the product stream from said reactor is recycled back and is cooled by a cooler (not shown in FIG. 1) in the recycle line before such recycle. The second carboxylation reactor (4) has no recycle like the first one. Apart from heat originating from the first carboxylation reactor (4) and as contained in the feed stream to the second carboxylation reactor (4), no heat is transferred to said feed stream before entering said second reactor.

The product stream (6) from the second carboxylation reactor (4), which comprises carbon dioxide, water, ethylene carbonate and catalyst, is sent directly to the first of two hydrolysis reactors (7) connected in series. In the hydrolysis reactors (7), ethylene carbonate is reacted with water to form ethylene glycol and carbon dioxide. Carbon dioxide is removed from the first hydrolysis reactor (7) as carbon dioxide stream (8) which is recycled to the first carboxylation reactor (4). The product stream (9) from the second carboxylation reactor (4) comprises water, ethylene glycol and catalyst. Upon removal of water and catalyst, ethylene glycol may be recovered.

The invention is further illustrated by the following Examples.

EXAMPLES

Figure 2:
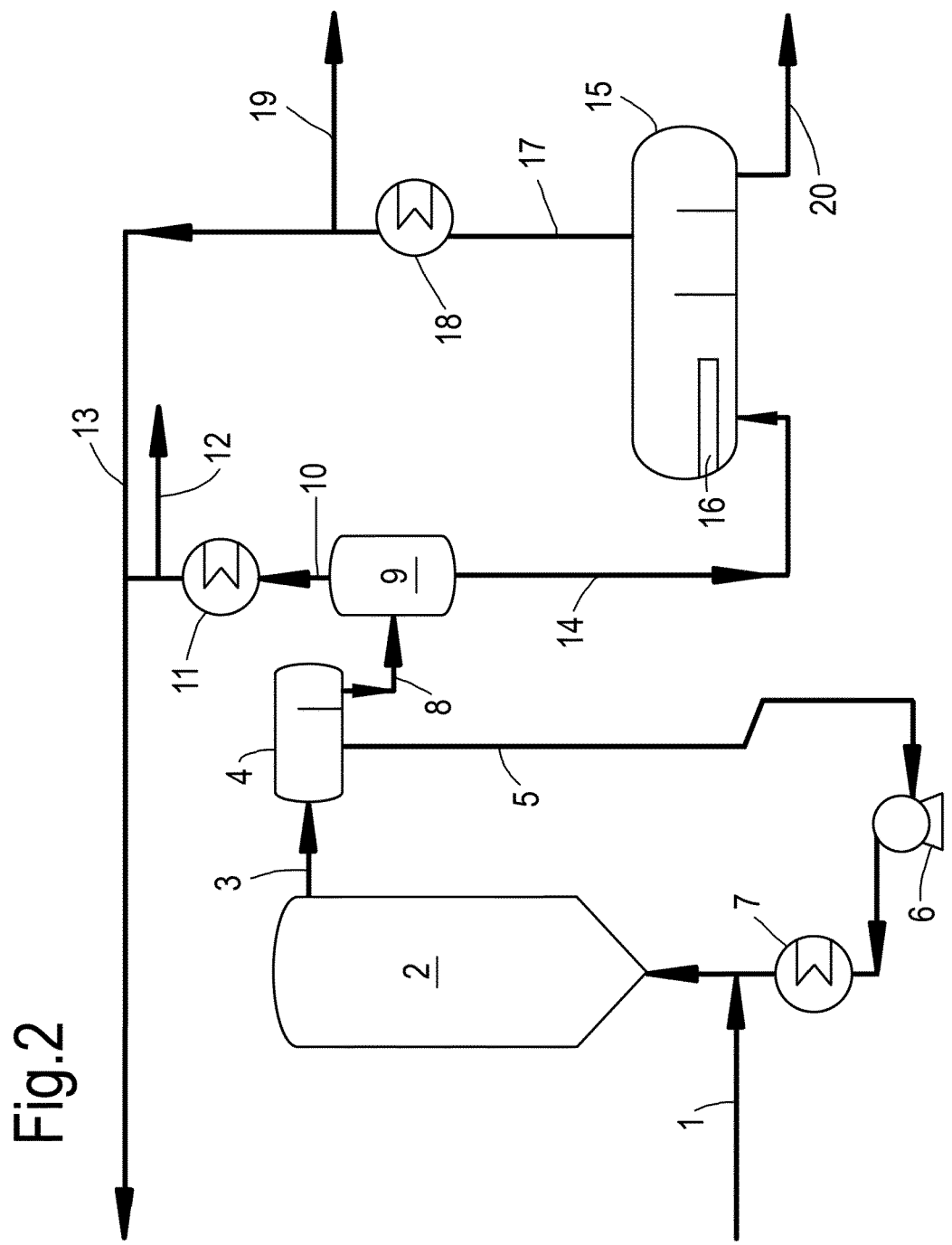
FIG. 2 shows a line-up for a process carried out in the Examples below which was not in accordance with the present invention.

In the present Examples, first a process was carried out using the line-up shown in FIG. 2 which process was not in accordance with the present invention, after which the process was modified such that it was in accordance with the present invention.

Referring to FIG. 2, a stream (1) comprising ethylene oxide, carbon dioxide, water, ethylene carbonate, ethylene glycol and diethylene glycol was fed to a vertical second carboxylation reactor (2). Further, said feed stream contained a catalyst which was a catalyst system comprising an iodide catalyst (carboxylation catalyst) and potassium carbonate (hydrolysis catalyst).

Said feed stream (1) originated from a vertical first carboxylation reactor (not shown in FIG. 2) wherein part of the product stream from said reactor was recycled back to said same reactor and was cooled by a cooler in the recycle line before such recycle. The feed stream (1) to the second carboxylation reactor (2) had a temperature of 129° C. and was not heated before entering the reactor. In the carboxylation reactors, ethylene oxide was reacted with carbon dioxide to form ethylene carbonate.

The product stream (3) from the second carboxylation reactor (2) was sent to a first vapour/liquid separator (4). Part of the product stream (3) was then recycled back via recycle line (5) to the second carboxylation reactor (2), using a circulation pump (6), and was heated by a first heater (7) in the recycle line (5) before such recycle to increase the temperature by about 4° C. Feed stream (1) and the stream in recycle line (5) were combined before entering the second carboxylation reactor (2). The non-recycled part (8) of the product stream (3) had a temperature of 146° C. and comprised ethylene oxide, ethylene carbonate, ethylene glycol, diethylene glycol, carbon dioxide, water and above-mentioned catalyst system. The non-recycled part (8) of the product stream (3) was sent to a second vapour/liquid separator (9). The separated vapour (10) was condensed in a first cooler (11). The condensed liquid was returned to the vapour/liquid separator (9). A purge stream (12) was removed from the process to prevent the build-up of impurities and inerts in the carbon dioxide which is recycled in the process. Further, the vapour comprised carbon dioxide, water and traces of ethylene oxide, which was recycled to the first carboxylation reactor via recycle line (13).

The liquid (14) separated by the second vapour/liquid separator (9) and having a temperature of 135° C. was fed to the bottom of a horizontal first hydrolysis reactor (15). The first hydrolysis reactor (15) was a baffled reactor which had 3 compartments formed by 2 vertical internal baffles. The first compartment wherein the liquid was fed contained a second heater (16) in the bottom. In the first hydrolysis reactor (15), ethylene carbonate was reacted with water to form ethylene glycol and carbon dioxide. Thus, carbon dioxide was produced within the first hydrolysis reactor (15), which left said reactor as a vapour stream (17) via an outlet in the top. Said vapour was condensed in a second cooler (18). The resulting condensed liquid (19) was partially returned to the first hydrolysis reactor (15) and partially purged. Further, the vapour comprised carbon dioxide and water, which was recycled together with the vapour resulting from the first cooler (11) to the first carboxylation reactor via recycle line (13).

The liquid product stream (20) leaving the first hydrolysis reactor (15) via an outlet in the bottom of the third compartment of the reactor comprised ethylene carbonate, ethylene glycol, diethylene glycol, carbon dioxide, water and above-mentioned catalyst system. The liquid product stream (20) from the first hydrolysis reactor (15) had a temperature of 150° C. and was fed to a second hydrolysis reactor (not shown in FIG. 2) which was similar to the first reactor but which did not contain a heater.

Then the following change was applied to the above-described reaction system. The first heater (7) and the circulation pump (6) in the recycle line (5) for the second carboxylation reactor (2) were switched off. This implied that there was no heated inlet stream to the second carboxylation reactor (2). Surprisingly, even though there was no recycle inlet stream to the second carboxylation reactor (2) and consequently no heating of such inlet stream before entering the reactor, the temperature increase over the second carboxylation reactor (2) did not change. Such temperature increase is a measure of ethylene oxide conversion.

Thus, surprisingly, by not sending a heated inlet stream to the second carboxylation reactor (2) as a result of switching off the first heater (7) and the circulation pump (6) in the recycle line (5) for the second carboxylation reactor (2), the ethylene oxide conversion was advantageously not affected. This is surprising as it would be expected that by not heating (part of) the feed to the second carboxylation reactor (2), the ethylene oxide conversion in that reactor would decrease.

The foregoing surprising finding implies advantageously that said first heater (7), circulation pump (6) and recycle line (5) for the second carboxylation reactor (2) are not needed and may therefore be omitted resulting in a simplification of the overall ethylene glycol production process and thus in lower capital expenditure. This is shown in FIG. 3.

Figure 3:
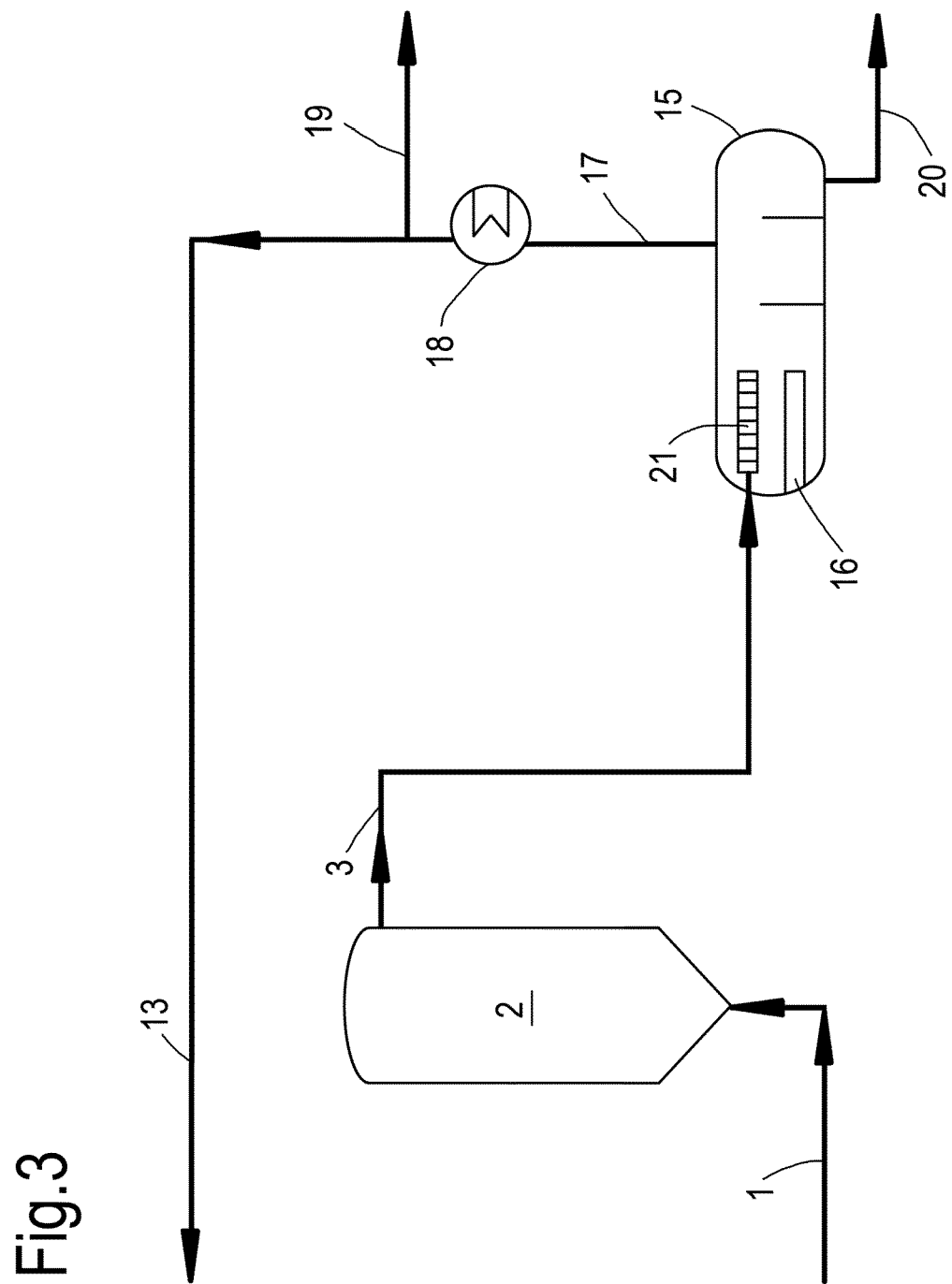
FIG. 3 shows a line-up for a process which is in accordance with the present invention.

In the process as shown in FIG. 3 the product stream (3) from the second carboxylation reactor (2) is not recycled to said same reactor but is sent directly to the first hydrolysis reactor (15). This implies that in the process as shown in FIG. 3, the first and second vapour-liquid separators (4) and (9), the recycle line (5), the circulation pump (6) and the first heater (7) in said recycle line, and the first cooler (11) as shown in FIG. 2 are advantageously omitted.

Further, in the process as shown in FIG. 3 the product stream (3) from the second carboxylation reactor (2) is not fed to the bottom of the first compartment of the first hydrolysis reactor (15), but to the top thereof above the liquid level (i.e. in the vapour cap). In addition to the heater (16) in the bottom, the first compartment also contains a vapour-liquid separator (21) in the top. The resulting vapour stream comprising carbon dioxide is removed, together with carbon dioxide produced in the first hydrolysis reactor, as vapour stream (17) via an outlet in the top as described above with reference to FIG. 2. The resulting liquid stream comprising ethylene carbonate is converted in the first hydrolysis reactor (15) thereby producing ethylene glycol and carbon dioxide as described above with reference to FIG. 2.

We claim:

1. Process for the preparation of ethylene glycol, comprising:
    a) converting a stream comprising ethylene oxide in the presence of a catalyst and carbon dioxide in two or more reactors to a stream comprising ethylene carbonate; and
    b) converting ethylene carbonate from the stream comprising ethylene carbonate obtained in step a) in the presence of a catalyst in one or more reactors to a stream comprising ethylene glycol and a stream comprising carbon dioxide,
    wherein an outlet stream from the first reactor of the two or more reactors used in step a) is split, one split sub-stream is sent to the next reactor in series and another split sub-stream is recycled to the first reactor;
    wherein the inlet stream or inlet streams to at least the last reactor of the two or more reactors used in step a) is or are not heated; and
    wherein an outlet stream comprising ethylene carbonate from the last reactor of the two or more reactors used in step a) is sent, without recycling a portion thereof to the last reactor used in step a), to the first reactor of the one or more reactors wherein step b) is carried out.

2. Process according to claim 1, wherein step a) is carried out in two or more reactors connected in series, and the inlet stream or inlet streams to the last reactor of the two or more reactors is or are not heated.

3. Process according to claim 1, wherein at least a portion of the outlet stream or outlet streams from the first reactor of the two or more reactors used in step a) is or are cooled.

4. Process according to claim 1, wherein the outlet stream comprising ethylene carbonate from the last reactor of the two or more reactors used in step a) is sent directly, without recycling a portion thereof to the last reactor used in step a), to the first reactor of the one or more reactors wherein step b) is carried out.

5. Process according to claim 1, wherein the split substream that is recycled to the first reactor used in step a) is cooled before recycling.

6. Process according to claim 1, wherein the inlet stream or inlet streams to at least one reactor of the two or more reactors used in step a) is or are not cooled.

7. Process according to claim 1, wherein the inlet stream or inlet streams to the last reactor of the two or more reactors is or are not cooled.

8. Process according to claim 2, wherein step a) is carried out in two reactors connected in series, and the inlet stream or inlet streams to the last reactor of the two reactors is or are not heated.

\* \* \* \* \*